United States Patent [19]
Alpern et al.

[11] Patent Number: 5,392,917
[45] Date of Patent: Feb. 28, 1995

[54] EASY OPEN 1-2-3 INSTRUMENTATION PACKAGE

[75] Inventors: Marvin Alpern, Glen Ridge; Teresa M. Simons, Piscataway, both of N.J.; Robert Cerwin, Pipersville, Pa.; Robert J. Kalinski, Milford, N.J.; Michael D. O'Toole, Suffern, N.Y.

[73] Assignee: Ethicon, Inc., Somerville, N.J.

[21] Appl. No.: 101,481

[22] Filed: Aug. 3, 1993

[51] Int. Cl.⁶ .................................................. B65D 1/34
[52] U.S. Cl. .................................. 206/570; 206/370; 206/440
[58] Field of Search ............... 206/363, 570, 370, 440, 206/438, 564; 229/125.35, 160.2, 123.1

[56] References Cited

U.S. PATENT DOCUMENTS

| | | | |
|---|---|---|---|
| 2,897,962 | 8/1959 | Zackheim | 229/125.35 X |
| 3,054,679 | 9/1962 | Bradford | 229/125.35 X |
| 3,697,223 | 10/1972 | Kovalcik et al. | 206/370 X |
| 3,730,338 | 5/1973 | Chesky | 206/570 X |
| 4,042,109 | 8/1977 | Barcan | 206/440 |
| 4,523,679 | 6/1985 | Paikoff et al. | 206/570 X |
| 4,673,085 | 6/1987 | Badouard et al. | 229/125.35 X |
| 4,844,251 | 7/1989 | Gueret | 206/440 X |
| 4,925,047 | 5/1990 | Valentine et al. | 206/570 X |
| 4,928,830 | 5/1990 | Brewer | 206/438 X |
| 4,946,038 | 8/1990 | Eaton | 229/125.35 X |
| 5,170,902 | 12/1992 | Wilson | 206/570 X |

*Primary Examiner*—Jacob K. Ackun, Jr.
*Attorney, Agent, or Firm*—Paul A. Coletti

[57] ABSTRACT

A novel surgical instrumentation kit is provided. There is a sterile reloading unit package in this kit. These reloading units or other separate packages may be maintained in their own sterile environment. Further, the ability of the surgeon to transfer from an endoscopic procedure to an open procedure is provided. Finally, there is described a novel package which allows the surgeon to rapidly open the tray and remove from it a surgical drape containing the instrumentation of the above-described kit.

7 Claims, 4 Drawing Sheets

5,392,917

EASY OPEN 1-2-3 INSTRUMENTATION PACKAGE

FIELD OF THE INVENTION

This invention relates to surgical instrumentation kits in which there is contained a reloadable instrumentation unit such as a surgical stapler cartridge or the like.

BACKGROUND OF THE INVENTION

Instrumentation kits have increased in popularity for performing surgical procedures. These instrumentation kits typically contain any number of surgical devices which enable a surgeon to perform a specific form of surgery. For instance, in a cardiovascular instrumentation kit, the surgeon may be capable of performing open heart surgery. In contrast, a bowel surgical instrumental kit may allow the surgeon to perform a surgical anastomosis.

Heretofore, these instrumentation kits have been contained in one sterile package. This may result in the contamination of an entire surgical instrumentation kit even though not all of the instruments are used. This may be especially true if a surgical instrumentation kit combines a surgical instrument with a reloadable unit such as a cartridge. Furthermore, it has been realized no previous surgical instrumentation kits have contained reloadable units, such as cartridges. It has, rather, been the hospital's responsibility to provide these reloading units separately from the surgical instrumental kits.

Moreover, none of the present surgical instrumentation kits provide for a drug applying mechanism, or a package containing sutures. Neither of these have been provided, because it has always been felt that the use of such mechanisms would be supplied in the operating room, and not necessarily as a requirement for performing the surgery. Thus, previously, surgical instrumentation kit suppliers have not included instruments such as sutures and/or drug applying mechanisms in their kits.

SUMMARY OF THE INVENTION

The present instrumentation kit makes available, in various combinations, equipment which enables surgeons to perform surgery and yet conserve sterility, if desired. Thus, in the surgical instrumentation kit of the present invention there is included at least one preloaded reloadable surgical instrument and which also contains at least one reloadable cartridge capable of being loaded into the surgical instrument. Also, this reloadable cartridge may be placed in a separate sterile package so that its sterility is guaranteed, independent of the sterility of the package in which the surgical kit is contained. Further, there may be provided a drug applying mechanism in this kit which contains a sterile container loadable into the drug applying mechanism. Moreover, to enable surgery to take place with respect to a particular patient there may be provided a disposable endoscope. The instrumentation kit may also contain instrumentation or accessories to provide for this potential or conversion from an endoscopic procedure to an open procedure. Finally, there may be .provided a kit containing sutures within the surgical instrumental kit. This allows the sterility of the sutures to be maintained independent of the sterility of the surgical instrumentation kit.

In a particularly preferred embodiment, a novel surgical package is provided which enables the user to easily and readily open the kit for its usage within the operating room. This package contains three flaps each of which flap one over the other. These flaps are provided so that the user may rip open the kit along one side, and then along two perpendicular sides. This causes the kit to be fully displayed in the operating room without the necessity of changing the position of the kit after it has been opened.

The foregoing features of the present invention will be more readily apparent and may be understood by referring to the following detailed description and illustrative embodiment of the invention and its associated packaging device, taken in connection with the description of the drawings which follow.

DETAILED DESCRIPTION OF THE INVENTION

Figure 1:
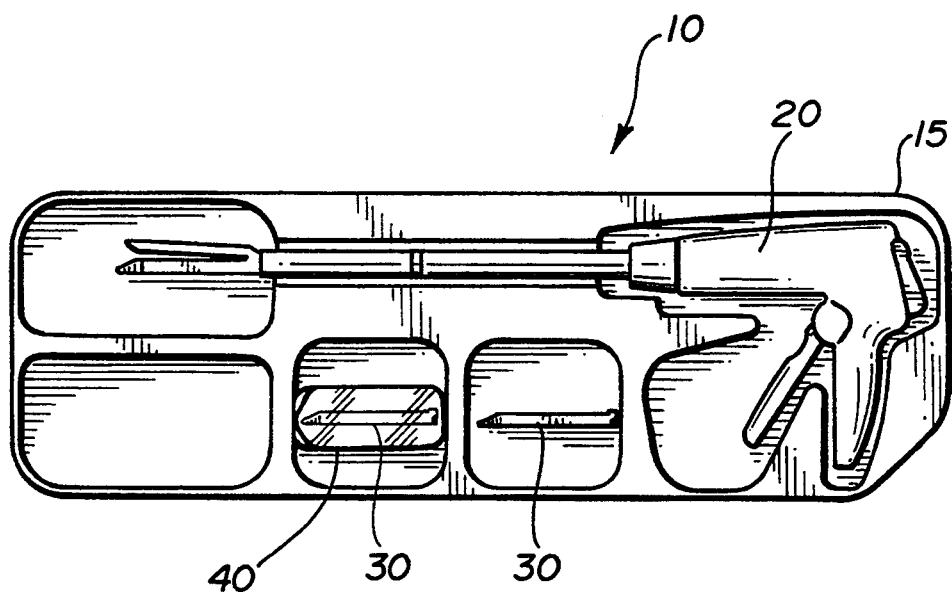
FIG. 1 shows a top plan view of a surgical instrumentation kit which contains a reloadable cartridge.

As seen in FIG. 1, there is contained a kit 10 which contains a surgical stapler 20, more particularly, an endoscopic linear cutter type stapler such as the ELC 60 (Ethicon Endo-Surgery, Cincinnati, Ohio) said stapler being preloaded with a cartridge, which further contains a package of reloadable cartridges 30. The stapler 20 and cartridges 30 are contained within a blister package formed from plastic and sealed with a typical Tyvek TM lid, well known in the industry. Importantly, one of the reloadable cartridges 30 as seen in the instrumentation kit 10, are contained in its own separately sealed package 40. This package 40 is sterile independent of the sterility of the blister package 15 containing the surgical instrumentation kit.

Thus, when the surgeon opens the blister package 15 to remove the surgical stapler 20, the reloadable cartridge unit 40 remains sterile. If the surgical instrumentation kit 10 is used but the cartridge 30 in package 40 is not, the cartridge 30 continues to be sterile. Thus, these separately sealed cartridge units 40 may be saved for use on the next patient, and a cost savings as well as a packaging savings is realized. In previous surgical instrumentation kits, once the kit package 15 was opened, these reloadable units 30 would have to be discarded as non-sterile, even if never used.

Figure 2A:
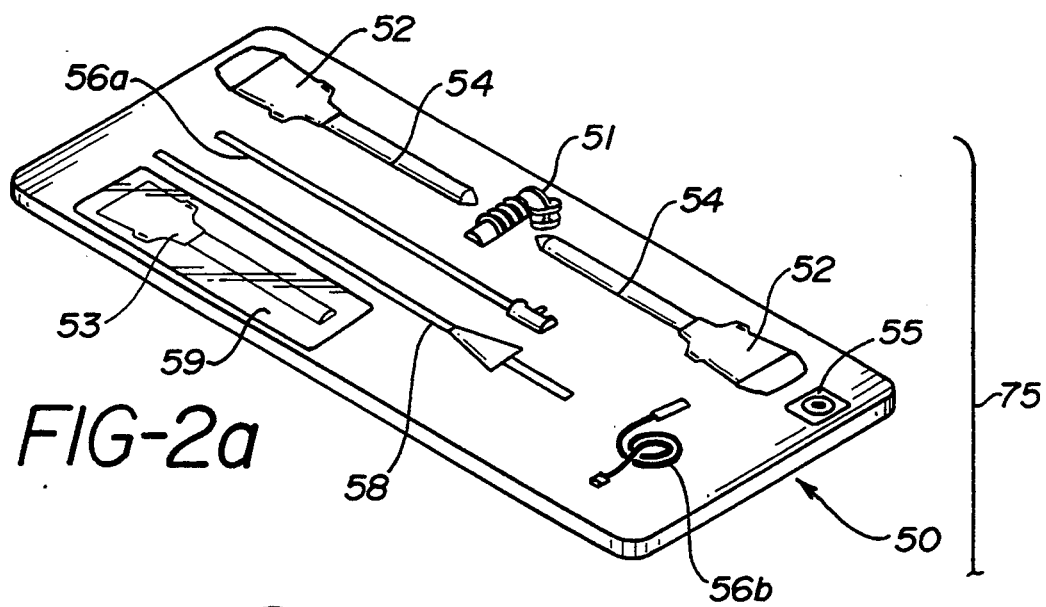
FIGS. 2a, 2b and 2c contain a series of flexible package trays each of which contain surgical instrumentation kits.
Figure 2B:
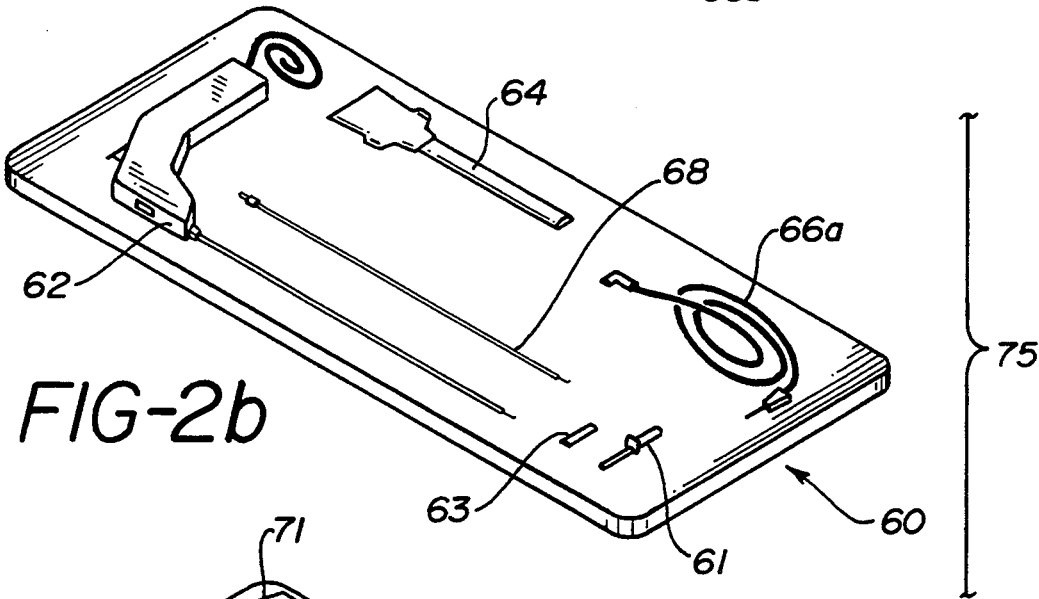
Figure 2C:
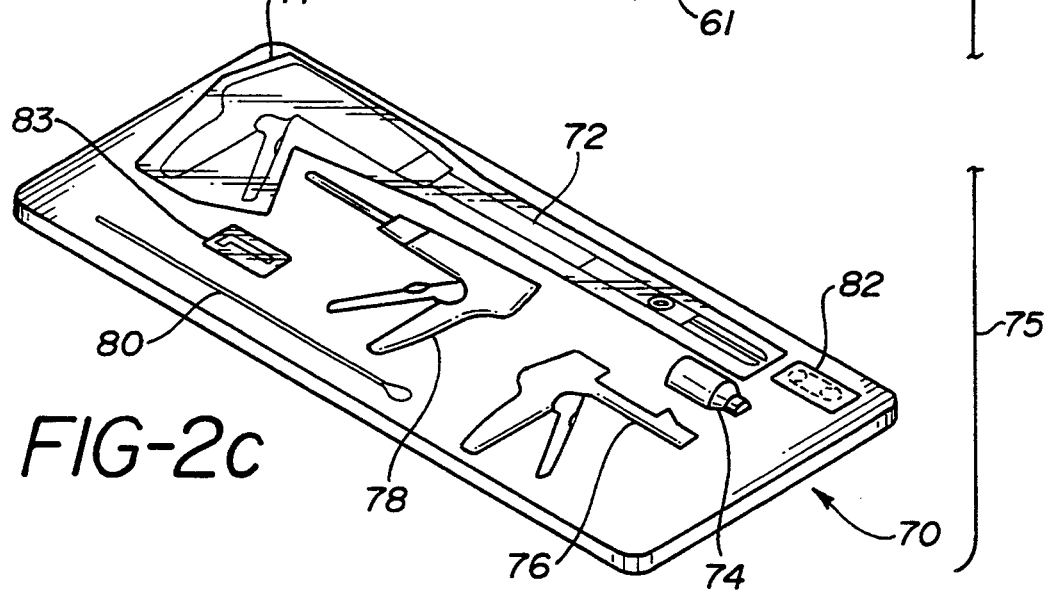

As further seen in FIGS. 2a, 2b and 2c a kit 75 formed from a series of nested flexible package trays 50, 60, 70 are provided, each of such trays being independently sterile. Each of these trays may enable a surgeon to perform a very complex surgery. Each of these trays 50, 60, 70 nests so that they fit one into the other, and each of the trays 50, 60, 70 is itself sterile, as well as the entire package in which the kit 75 is contained. On the first level 50 of the kit 75, there is contained two trocars 52 in sleeves 54, (Endopath TM, Ethicon Endo-Surgery) a disposable endoscope 56a, 56b, a Verress-type needle 58 (an insufflation needle), stabilizer 51, an extra trocar sleeve 53 and a reducer cap 55 which provides an optional seal for smaller instrument shafts, one of which is ideally 10 to 11 mm and the other which is ideally 5 mm in diameter. Each of these devices is, of course, well known in the art.

On the second nested tray there is contained an electro-cautery instrument 62, (Probe Plus, Ethicon Endo-Surgery) and a 5 mm trocar sleeve 64. Optionally these may include a morcellating instrument (not shown). There is further contained accessories for the disposable scope 56a and/or the electro-cautery instrument 62. These may comprise such things as a power cord 66a, a banana jack 61, an electrosurgery shaft and probe 68 and a lens cover 63, such as a glare eliminating device. The second package 60 is contained in its own sterile environment so that, again, if the surgeon never uses any of the elements in the primary package, this second package maintains sterility for use on a different patient, so that a cost savings is realized.

Furthermore, as described in connection with FIG. 1, each of the instruments contained in either of these trays may further be placed in its own sterile package, if it is foreseen that some of these instruments may not be necessary in order to perform a particular surgery. For instance, one of the trocar sleeves 53 is seen contained in its own sterile package 59.

Finally, on the third level 70 of the flexible package tray 75 there is contained an articulating instrument such as an articulating endoscopic linear cutter stapler 72 (Ethicon Endo-Surgery). Such a flexible instrument useful for many different surgical purposes may be contained in its own flexible package 71. Moreover, there is contained a sterile drug container 74 such as Interceed TM (anti-adhesion drug) and drug applicator 76. There may also be contained a skin stapler 78 (Proximate RH, Ethicon Endo-Surgery). As further can be seen on the third package level there is an Endoloop applicator 80, also made by Ethicon Endo-Surgery. There is included a reload cartridge 83 contained in its own sterile package, for use with the stapler 72. Finally, there may be contained a suture packages 82 (Vicryl TM or PDS TM, Ethicon, Inc., Somerville, New Jersey) which are maintained sterile in and of themselves.

This kit 75, therefore, enables the surgeon to perform any conceivable facet of an abdominal stomach resectioning surgery. Whatever is encountered by the surgeon during the surgery, each of the instruments in kit 75 are there, ready for use. However, if some of the instruments are not used, they can be saved for the next patient, because these instruments are, indeed, sterile. This may encompass one of the trays 50, 60, 70, or alternately, a package such as the packages 53, 71, 82 or 83.

Figure 6A:
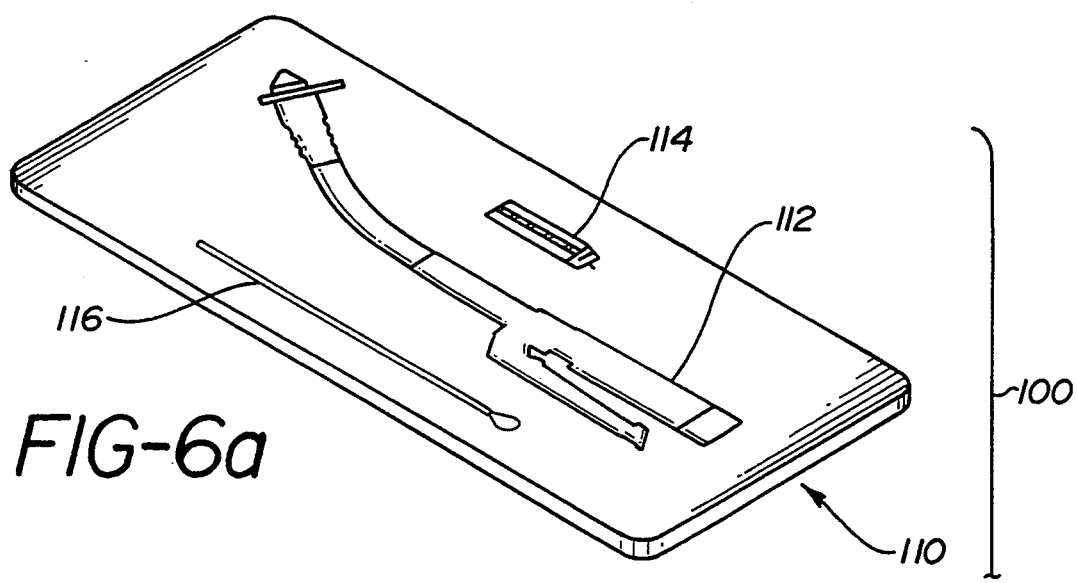
FIGS. 6a, 6b and 6c describe a kit particularly described for a bowel anastomosis.
Figure 6B:
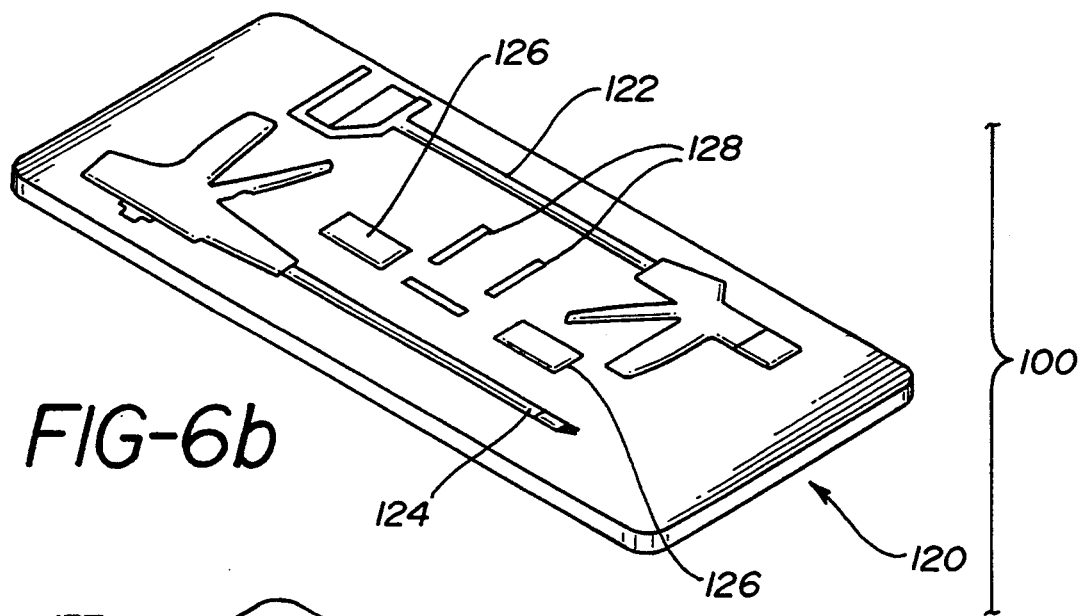
Figure 6C:
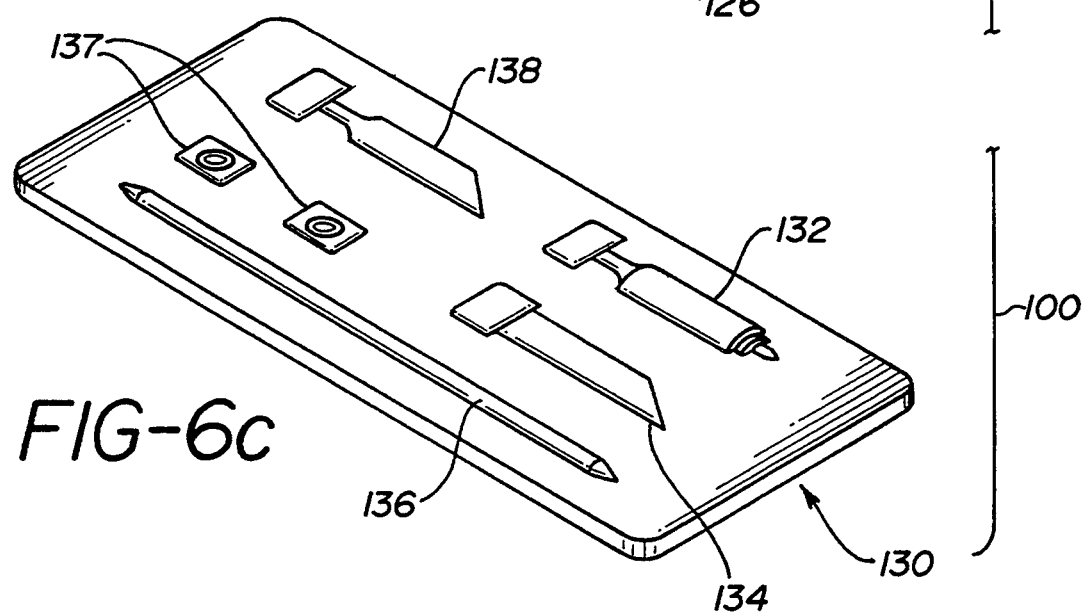

Turning to FIG. 6a, 6b and 6c, there is contained a surgical bowel kit 100 which also contains a series of three trays 110, 120, 130. The first tray 110 contains a circular stapler 112 (Proximate Circular, Ethicon Endo-Surgery), a purse stringing device 114 and an Endoloop TM applier 116. The second tray 120 contains a linear stapler 122 and a multiple clip applier (Ligaclip ERCA) 124 as well as a sterile suture packages 126, 128. This multiple clip applier is capable of multiple firings without reloading. The third tray 130 contains a kit for a 33 mm trocar, such as the 33 mm trocar and related accessories sold by Ethicon Endo-Surgery, Cincinnati, Ohio. These encompass obturator 132, sleeve 134, exchange rod or dilator 136, reducers 137 and tissue extractor 138.

Endoscopic surgical procedure require that a surgeon learn significant new skills and techniques. This learning curve as well as many unforeseen complications can result in conversion of an endoscopic procedure to an open incision procedure during the procedures progress. For example, an endoscopic low colon resection using a circular stapler may require conversion due to complications such as internal bleeding. The patient is opened using an abdominal incision and the complication is remedied utilizing the improved access. With this improved access, the surgeon may prefer to use an open procedure purse string instrument to reduce the complexity and time in applying the purse string for the circular stapling instrument. The open purse string instrument is included in the kit and provides the added assurance that no time will be lost applying a manual purse string or searching for the instrument in the stock room. Optionally, the open purse string device may be packaged in a separate sterile package so it can be saved for later use in another patient.

This circular bowel kit 100 enables the surgeon to perform either an open or endoscopic surgery at a moment's notice. Thus, if a surgeon must open the body, the surgeon is able to rapidly convert from an endoscopic procedure (using tray 130) to an open procedure (using trays 110, 120) without having to order and have available in the operating room a separate kit for both procedures. This "combined" kit enables the surgeon to have the immediate choice of performing either an open or an endoscopic procedure.

Figure 3:
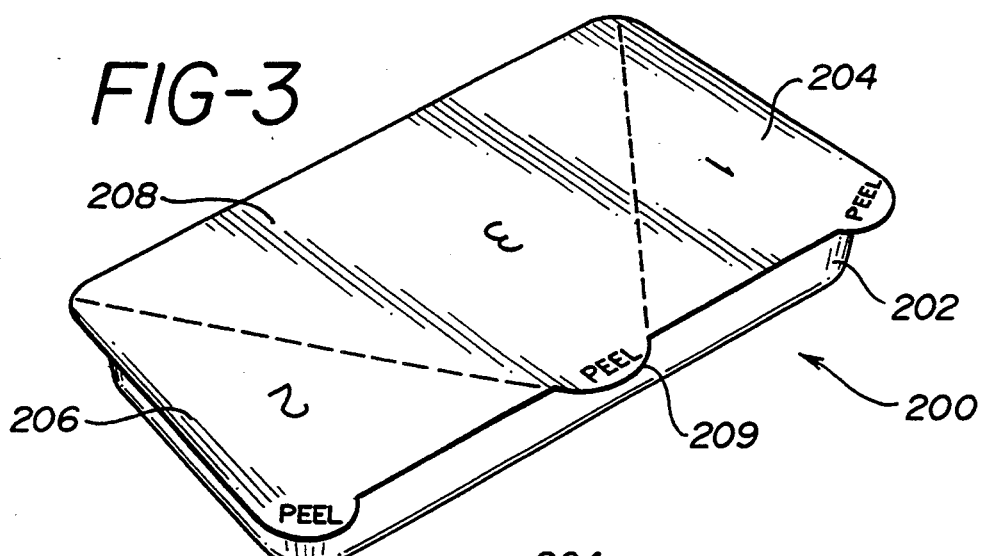
FIGS. 3, 4 and 5 are perspective views of a package in which the instrumentation kit of the present invention may be contained.
Figure 4:
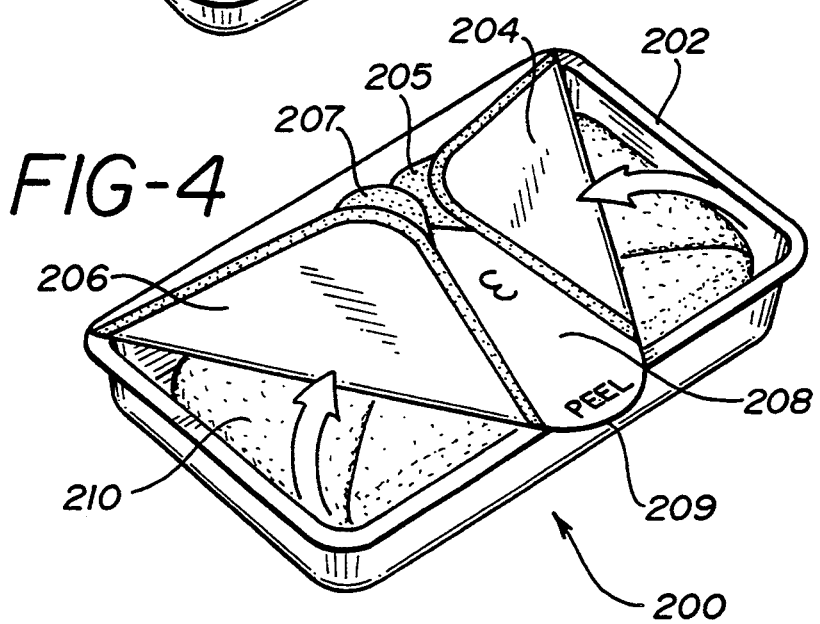
Figure 5:
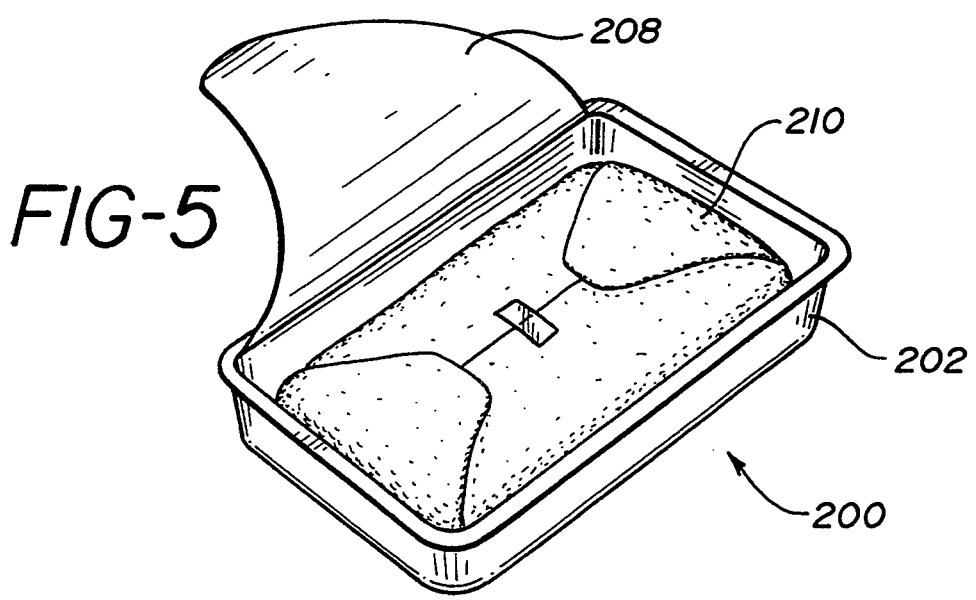

As seen in FIGS. 3, 4 and 5 there is contained a novel sterile package 200 which may contain one of these kits. As in FIG. 3, this package is commonly referred to as the "1-2-3 Peel-Open TM package. It is seen that there is contained a tray 202 which contains a triple folded lid 204, 206, 208 adhesively sealed to the opening in package tray 202. This triple folded lid is formed so that it may be opened on either side 204, 206, along the score lines provided on either the left or the right side first. This is done by pulling on the tabs 201, 203 at either end of the tray. Then the nurse will open the opposite side to form the configuration of FIG. 4. Once the corners of the lid 205, 207 are folded back along the score lines and adhesively secured to the lid, it is now easy to open the center portion 208 of the lid at tab 209. This configuration may prove valuable for a person with short arms, who is unable to reach around the entire box which in some instances may be 20–30 inches in width.

Contained within the sterile package 200 there is a surgical type drape 210. This surgical drape 210 may be removed from the tray so that it is placed on a surgical stand. Then, the tape 212 is removed and the package is opened up so that the kit 100 itself is placed on the stand in a ready-to-use position. Thus, time and cost are saved from use of previous kits, which would have had to have been placed on a surgical drape provided from different sterile package and onto the stand. Now, because the surgical drape 210 is included in the sterile package 200, there is no need for separate packaging of this material.

It will be seen that this package therefore enables any of the previously mentioned kits to be placed therein without need of resterilizing or waste of product. However, it is also realized that the sterile packages such as packages 53, 71, 82 or 83 contained within the sterile kit enables the user to selectively operate the kit and then, if there are sterile packages remaining after the procedure is over, save these for future usage. This is in sharp contrast to the aforementioned discarding of surgical suture packages previously done in any surgical procedures.

Thus, there are provided a number of useful inventions in this device. First, the concept of a sterile instrumentation kit contained within a sterile surgical instrumentation kit is provided. Second, the concept of using a reloadable cartridge contained in its own sterile kit is provided. Third, the concept of providing a novel package which contains a 1-2-3 opening procedure is maintained. Finally, the concept of using various novel instrumentation packages such as a surgical tray within the surgical package is provided. Each of these useful innovations allows the surgeon to have greater flexibility to perform a typical procedure, to convert from one procedure to another (such as from an endoscopic procedure to an open procedure), and to have a cost effective savings by being able to transfer one sterile package to another separate procedure on a separate patient.

It will be realized that this invention can be realized from the appended claims and their equivalents.

We claim:

1. A surgical package comprising:
    a tray having at least one surgical instrument containing portion and an opening in said surgical instrument containing portion defining the outer periphery of said tray, said opening generally quadrilateral in shape; and
    a unitary triple folded lid adhesively attached to said opening, said lid having three portions and a pair of score lines about which two portions of said lid may be folded onto a third portion of said lid to thereby create a triple fold, and said lid having at least two corner pull tabs located on at least two corners defining a side of said quadrilateral shaped opening in said tray and at least one central pull tab located between said two pull tabs on said defined side and wherein said lid is attached to said opening exclusively on the periphery of said opening.

2. The package of claim 1 further comprising said pair of score lines extending divergently from said central pull tab toward a side opposite said defined side of said quadrilateral shaped opening.

3. The package of claim 1 wherein said corner pull tabs contain adhesive surfaces to secure said corner pull tabs to an opposite side of cover.

4. The package of claim 1 in combination with a plurality of surgical instruments placed in said tray and wherein said instruments are contained in a surgical drape surrounding said instruments.

5. A surgical package containing a tray, said tray having an opening sealed by a lid, and at least one surgical instrument contained in said tray, said surgical instrument wrapped in a surgical drape and wherein said instrument and drape are removable from said tray; and
    wherein said opening is quadrilateral in shape and said lid has at least two corner pull tabs located on at least two corners defining a side of said quadrilateral shaped opening and at least one central pull tab located between said two pull tabs on said defined side.

6. The package of claim 5 further comprising a pair of score lines extending divergently from said central pull tab toward a side opposite said side of said quadrilateral shaped opening.

7. The package of claim 5 wherein said corner pull tabs contain adhesive surfaces to secure said corner pull tabs to an opposite side of said cover.

* * * * *